United States Patent [19]
Chou

[11] Patent Number: 5,354,294
[45] Date of Patent: Oct. 11, 1994

[54] COMBINATION REFLECTANCE FIBER OPTIC LASER BEAM ANGLE DELIVERY

[75] Inventor: Marilyn M. Chou, Piedmont, Calif.

[73] Assignee: Xintec Corporation, Oakland, Calif.

[21] Appl. No.: 87,981

[22] Filed: Jul. 7, 1993

Related U.S. Application Data

[63] Continuation-in-part of Ser. No. 67,566, May 26, 1993.

[51] Int. Cl.⁵ ............................................. A61B 17/32
[52] U.S. Cl. ........................................ 606/16; 606/17; 606/11
[58] Field of Search ................. 606/15, 16, 17, 10, 606/11, 12

[56]         References Cited
       U.S. PATENT DOCUMENTS

| | | | |
|---|---|---|---|
| Re. 32,849 | 1/1989 | Wei et al. | 204/192.27 |
| 4,309,075 | 1/1982 | Apfel et al. | 350/164 |
| 4,372,642 | 2/1983 | Singer et al. | 350/96.12 |
| 4,718,417 | 1/1988 | Kittrell et al. | 606/15 |
| 4,740,047 | 4/1988 | Abe et al. | 606/3 |
| 4,842,390 | 6/1989 | Sottini et al. | 606/15 |
| 4,925,259 | 5/1990 | Emmett | 350/1.6 |
| 4,940,636 | 7/1990 | Brock et al. | 428/426 |
| 4,950,268 | 8/1990 | Kink | 606/12 |
| 4,992,087 | 2/1991 | Holscher | 65/60.2 |
| 5,000,575 | 3/1991 | Southwell | 356/382 |
| 5,009,920 | 4/1991 | Lee | 427/9 |
| 5,057,099 | 10/1991 | Rink | 606/12 |
| 5,061,265 | 10/1991 | Abela et al. | 606/15 |
| 5,129,896 | 7/1992 | Hasson | 606/15 |
| 5,143,445 | 9/1992 | Bateman et al. | 362/293 |
| 5,160,668 | 11/1992 | Imris | 264/1.7 |
| 5,163,935 | 11/1992 | Black et al. | 606/17 |

FOREIGN PATENT DOCUMENTS

90/04249  2/1991  PCT Int'l Appl. ............ A61B 8/12

*Primary Examiner*—Peter A. Aschenbrenner
*Assistant Examiner*—Sonya C. Harris
*Attorney, Agent, or Firm*—James J. Leary; Ray K. Shahani

[57]           ABSTRACT

The present invention relates generally to a family of fiber optic laser beam angle delivery devices for use in medical and other applications, and more particularly, to such an apparatus wherein the transmitted radiation is delivered through and at various angles to the central axis of an optical fiber by reflection off of a combination of surfaces.

30 Claims, 6 Drawing Sheets

COMBINATION REFLECTANCE FIBER OPTIC LASER BEAM ANGLE DELIVERY

REFERENCE TO RELATED APPLICATION

This is a continuation in part of co-pending patent application Ser. No. 08/067566 filed May 26, 1993.

FIELD OF THE INVENTION

The present invention relates generally to a family of fiber optic laser beam angle delivery devices for use in medical and other applications, and more particularly, to such an apparatus wherein the transmitted radiation is delivered through and at various angles to the central axis of an optical fiber by reflection off of a combination of surfaces.

BACKGROUND OF THE INVENTION

Although the first useful lasers were developed in the 1960s, recent advances in laser and fiber optic delivery systems have greatly enhanced the use of this technology in the field of medicine. Today there are numerous types of laser systems designed for operation in a wide range of applications primarily related to surgical and other medical procedures.

A common type of laser known as a CO2 laser delivers radiation with a wavelength of 10.64 microns. However, in order to focus or channel the radiated energy produced by a CO2 laser it is necessary to configure sets of mirrors in certain ways. These systems are typically large and expensive. With the advent of the Nd:YAG type laser delivering electromagnetic energy at a wavelength of 1.064 microns, it became possible to generate and focus the laser radiation through a silica core optical fiber. Thus, fiber optic surgical tools have become important in certain procedures. The range of their utility is still being explored and discovered.

Laser fibers are used in different ways, including incision, necrosis or killing of live tissue, excision or removal of tissue and structure, and cauterization of tissue. A very focused beam would provide the greatest amount of control during either operation. Cauterization and necrosis of living tissue is accomplished by coagulation, or more precisely with respect to the laser itself, by photocoagulation of contacted or penetrated tissue. In this process the laser beam causes the proteins in the contacted tissue to heat up rapidly and thermally denature. This essentially kills living tissue and seals blood vessels. The process has been likened to frying an egg. In practice, during an incision procedure cauterization of the incised tissue is likely to occur simultaneously. Thus, laser surgery is often characterized by an absence of bleeding during the surgery.

In the prior art there are described devices which generate a dual wavelength beam of radiation and effect both cutting and cauterizing simultaneously. Such devices generally use one type of laser with some type of harmonic generator for providing half or double fundamental wavelength beams. There also exist inventions which deliver energy at much shorter wavelengths, such as 250-350 nm. At these wavelengths proteins, as opposed to water molecules, absorb the radiation. These systems, however, are less suitable for general types of surgical operations since they are more complicated to operate. Use of such systems has not become standard in most medical facilities and their cost is generally too high to justify their purchase for occasional use in fairly specialized procedures.

The construction of optical fibers used in surgical procedures is fairly simple. A quartz, plastic or silicone cladding is used to constrain the laser light to the quartz core. Theoretically, only a few of the entering photons are directed straight down the axis of the fiber. Transmission of the radiant beam is possible since the rest of the photons are constrained to the core of the fiber due to internal reflectance by the quartz cladding interface. Very few photons escape the fiber. The technology related to the use of silica core fibers in medical lasers is well known, e.g. B. P. McCann, Photonics Spectra, May 1990, pp 127-136.

Differences between these types of optical fibers and those used in telecommunications and data transmission are important. Several design factors must be considered such as sterilizability, quartz core integrity and purity, power capacity and index of refraction of materials of construction.

Generally, 10 to 100 watts of energy are used to perform soft tissue surgery. A fiber optic laser scalpel used externally might be operated much differently than one used in internal or endoscopic surgery. Some endoscopes have multiple channels to accommodate a viewing port or camera, a laser delivery device, and an irrigation supply and accompanying vacuum channel.

Delivery of high power radiation can have a very damaging effect on the fiber tip itself. One of the problems with existing designs is that the tip which directs the laser beam to a right angle becomes overheated. This is caused by an absorption of power (heat) at the reflecting surface. Overheating at or near the surface of the fiber tip can be caused by an accumulation of incompletely burned tissue which rapidly heats up and triggers a process known as thermal runaway. As heat builds up, the fiber tip gets hot and sometimes starts to melt or deform. Often, angle firing fiber optic surgical devices will need to be replaced partway through the surgical operation due to this problem.

Thus, the problems associated with currently available angle delivery fiber optic laser devices are mainly related to fiber overheating and failure. One solution would be to provide a transparent, hard, heat resistant tip, such as sapphire or quartz. An alternative is to provide a highly reflective surface in the scalpel tip for deflecting the beam.

This invention discloses a device wherein the end of the optical fiber is bias cut and, optionally, polished, and placed in intimate contact with a highly reflective mirrored surface. Depending on the application and operational parameters the instrument is designed around, it may be advantageous to bury the bias cut tip of the optical fiber into the reflective mirrored surface of the reflective cap or insert. Thus, the supplied laser radiation is reflected to the side and leakage of light near the interface between the fiber and the reflective surface is reduced or eliminated. Another embodiment of this invention provides the firing tip with a void or pocket of air at the end of a bias cut fiber. In this embodiment, the end surface of the firing tip might be coated with an interference film completely opaque to light at the wavelength of the laser beam.

An embodiment which has proved to be very effective is a truncated ball tip fiber having a bias cut through the ball portion providing a cut surface with a greater surface area than that of the fiber alone. When the tip is cut at an operative angle and polished, a laser beam is reflected internally to the side. The polished end surface can be placed in intimate contact with an efficient reflector such as a mirrored surface having a layer of gold or silver or other metal or material. The result would be to reflect any part of the laser beam which passed through the cut end surface and was not internally reflected. Additionally, the cut surface of the ball tip can be recessed or buried slightly in the reflective surface resulting in a device which transmits the laser beam in a defined angle without overheating or failing.

Another embodiment might have a reflective layer deposited directly onto the cut surface of the fiber. One material capable of being deposited in a very thin coating and producing a very high reflectance is gold. A protective layer over the reflective material could also be applied and be useful to add durability and thermal resistance to the reflective material. U.S. Pat. No. 4,992,087, incorporated herein by reference, discloses a reflective coating consisting of a metal or metal alloy and a process for applying it to a glass surface.

Multiple layer optical interference films, also known as interference filters or films, are well known in the art. Such films comprise alternating layers of two or more materials, typically one with a relatively high index of refraction and the other with a relatively low index of refraction. These materials are also known as dielectrics. Such are well known in the art and can be designed to reflect or transmit light radiation from various portions of the electromagnetic spectrum. Often, materials with high and low indices of refractivity are applied in alternating layers so as to comprise a "quarter wave stack", each layer having an optical thickness equal to approximately one quarter wavelength of the incident light wave. These types of reflectors have been described providing optical absorption losses of as little as 0.0001% to 0.0002%.

Methods for manufacturing these films are described in the prior art. U.S. Pat. No. 4,925,259, incorporated herein by reference, describes a damage-resistant dielectric coating formed over a silica substrate. Using a pulsed-plasma assisted chemical vapor deposition process several hundreds and even thousands of layer pairs can be deposited rapidly. Larger differences between the indices of refraction require a lesser number of layer pairs to obtain a given value of reflectance. In some cases, the indices of refractivity of alternating materials can be very similar and the number of layers very great. These coatings seem to have superior damage-resistance to optical radiation, approaching the damage resistance of pure silica. For laser applications using high power, components can be made to withstand high energy flux densities. They are also resistant to abrasion. Since the materials are very similar in composition there are fewer problems associated with differences in thermal and mechanical properties. Peeling and scaling is avoided as are microcracks which, in a given layer, would otherwise occlude the film.

At the reflecting surface, if most of the incident radiation is reflected very little will be absorbed and the temperature at the surface will not rise significantly. There is no known prior art providing an efficient reflector in intimate contact with the polished bias cut fiber tip surface, a reflective coating such as an interference film to internally reflect the beam of a laser used in conjunction with an optical fiber to perform surgical or other cutting or heating procedures, or a fiber tip with a sealed air pocket such that the laser light is reflected to the side based on the different indices of refraction of the optical fiber waveguide and the air or other gas or fluid in the pocket.

Clinical applications for this invention include surgical ablation, vaporization, incision, excision, coagulation and cauterization of tissue. These operations can be performed in air or in fluid, either in open or in endoscopic methods, through natural body channels or through artificial incisions. Other applications include scientific, industrial, entertainment, communications, and other commercial applications where angle delivery of laser beams via optical fibers at any wavelength is useful.

SUMMARY OF THE INVENTION

It is an object of this invention to provide a novel and efficient angle delivery fiber optic laser device for medical and other applications. In the present invention the transmitting end of the optical fiber is shaped and/or cut and polished at an angle to the central axis of the fiber. Thus, the precise angle at which the laser beam is directed, whether it be greater than, equal to or less than 90 degrees to the incident beam, can be specified. The embodiments described herein are referred to as combination reflectance devices referring to their ability to deliver laser power by reflectance from a combination of surfaces, including surfaces on the fiber itself as well as on a reflective cap or shell.

Once the tip of the fiber is contoured with a certain shape and polished to a certain angle, the fiber can be positioned in intimate contact with a mirrored surface. The mirrored surface can be on an insert held in place by a cap attached to the fiber. Thus, the laser beam would impinge upon the reflective surface to reflect up to 98% of the laser energy at an angle in relationship to the central axis of the fiber. Additionally, the cut surface of the fiber tip can be recessed or buried slightly in the reflective surface resulting in a device which is very efficient at transferring energy without overheating or failing or allowing light leakage.

A reflective interference coating may or may not be applied to the end surface of the fiber before assembly. Materials, or combinations of materials, and the thickness and order in which they could be applied to a surface would be known to one skilled in the art. Such an interference coating, almost 100% reflective at 1.064 nm, would be useful with an Nd:YAG laser. Furthermore, such coatings could be specified to provide reflectance at virtually any wavelength, allowing the invention to be used with other lasers.

Another embodiment of this invention would include encasing the bias cut portion of the fiber tip in a sealed air bubble or pocket. Since a polished bias cut fiber will, in air, reflect a light beam to the side as a function of the difference between indices of refraction of the optical fiber and air, a device thus constructed will be useful in fluid environments, thus emulating operation in air. The tip could also be filled with other types of gases or fluids which, upon proper design, would have the desired effect. The basic principle of this design lies in the selection of a medium with an index of refraction significantly lower than that of the optical fiber for placing in intimate contact with the fiber itself.

One useful embodiment of the invention would comprise a coaxial cooling system for the tip of the fiber. The cap or shell encasing a reflective insert can be attached to the tip of the fiber using a metallic bushing to increase the mechanical integrity of the connection to the fiber.

DETAILED DESCRIPTION OF THE INVENTION

The embodiments described herein are referred to as combination reflectance devices referring to their ability to deliver laser power by reflectance from a combination of surfaces, including surfaces on the fiber itself as well as on a reflective cap or shell.

Figure 1:
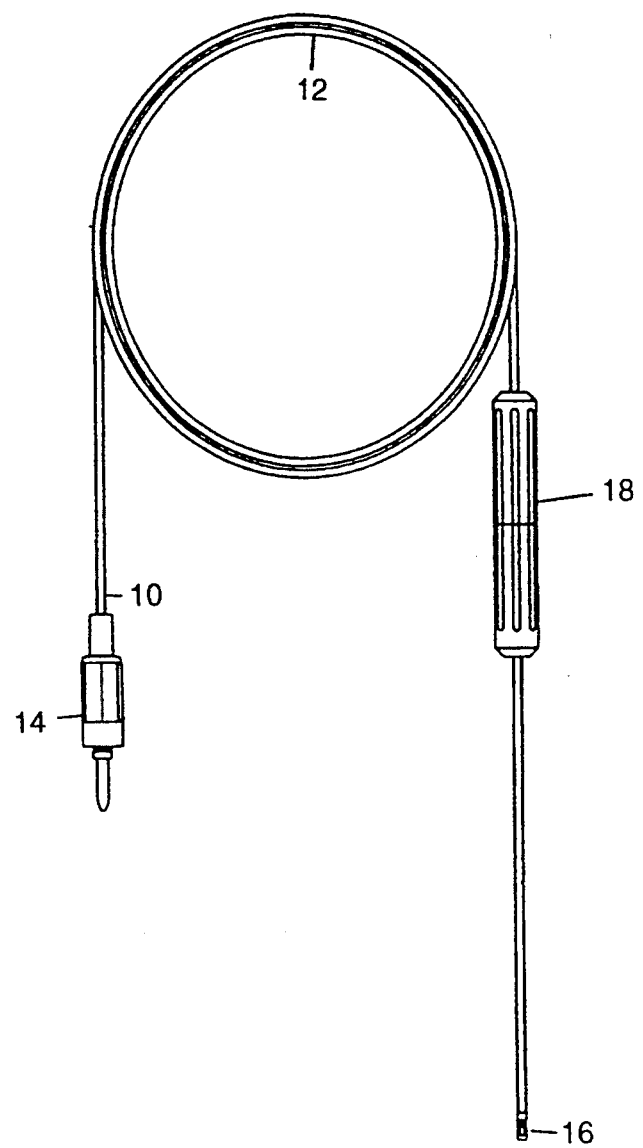
FIG. 1 is a schematic illustration of the present invention with a depth positioning device attached.

FIG. 1 is a view of the present invention, a laser beam angle delivery fiber optic device. At the receiving end 10 of the optical fiber 12 there is a releasable optical fiber connector 14. These connectors are standard in the industry and can also be proprietary. The fiber has an angle delivery tip 16.

Also shown is a positioning apparatus 18 for use when the device is inserted through the lumen of a viewing scope for certain types of procedures. The distance through which the fiber tip is inserted into a cannula or channel of an endoscope can be adjusted and precisely positioned by the surgeon during a surgical operation. It can also serve as a handle or gripping system for the fiber. One such apparatus would be made of two sections which screw together to tighten around the jacket of the optical fiber or untightened for repositioning with a slight twist.

Figure 2:
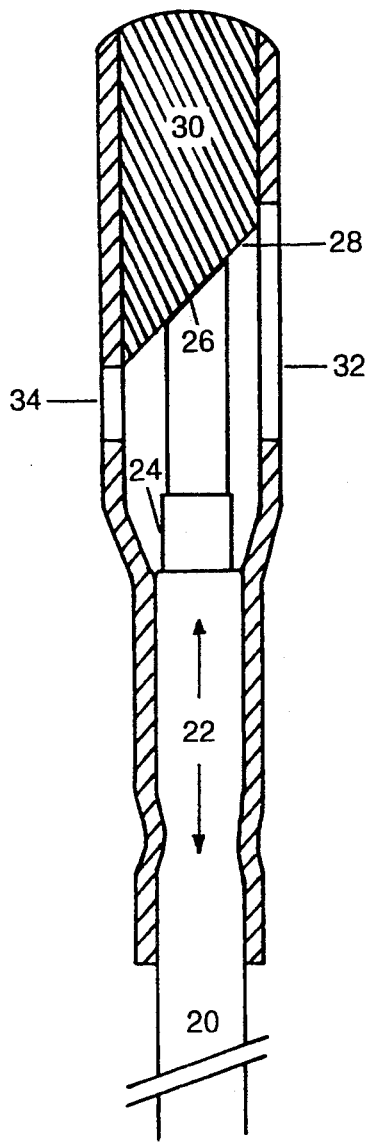
FIG. 2 is a cross section view of the transmitting end of a preferred embodiment of the invention.

FIG. 2 is a cross section view of a preferred embodiment of the angle delivery optical fiber tip. As shown, the fiber 20 is bias cut at an angle, other than perpendicular, to the central axis 22 of the fiber. The cladding of the fiber 24 is removed near the distal fiber tip. The bias end surface of the fiber 26 is in intimate contact with the mirrored reflective surface 28 of insert 30. The main laser beam delivery window 32 is oriented to an operative position with respect to the fiber and mirrored surface. A cooling vent 34 may or may not be provided. Thus, the mirrored reflective surface acts as both a heat sink and reflector during use. The cooling vent may or may not be used for irrigation fluid to be circulated around the fiber tip.

The surfaces in contact with each other could be complementarily countoured so as to provide a beam with a specific pattern. For example, the polished tip of the fiber, while cut at an angle to the fiber's central axis, might also have a generally convex shape in intimate contact with a reflective cap with a corresponding concavity. This would result in a beam which focused at a point beyond the fiber and then thereafter became divergent. Contoured surfaces might be spherical, parabolic, ellipsoidal, etc.

Figure 3:
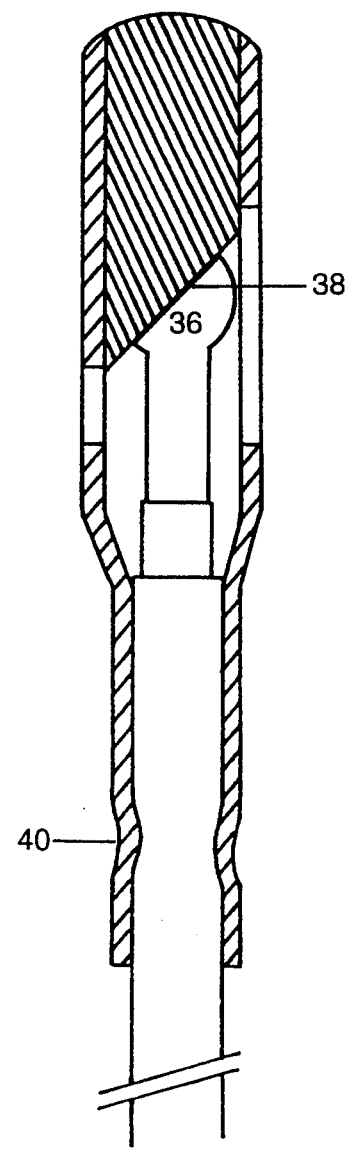
FIG. 3 is a cross section view of the transmitting end of another preferred embodiment of the invention, specifically showing the ball tip fiber end.

FIG. 3 is a cross section view of another preferred embodiment of the fiber tip. In this embodiment the optical fiber has a ball tip 36 which has been given a bias cut end surface 38. One way to make this truncated ball shaped tip would be to heat the end of a silica fiber. As the tip melts the molten silica will coalesce at the end and form a ball or drop of molten silica. Then, the ball can be given a bias cut and polished and placed in intimate contact with a reflective surface as FIG. 2. Also shown at 40 is a crimp in the part of the reflective shell in contact with the cladding of the fiber. This connecting means is important for maintaining mechanical integrity during operation, especially at elevated temperatures. A mechanical crimp, as shown, is effective when the shell is constructed of a suitable material such as a metal. Stainless steel is convenient to use. Other materials of construction include plastics or composites and these can be formed and connected together with high temperature processing, adhesives, clamps, etc.

Figure 4:
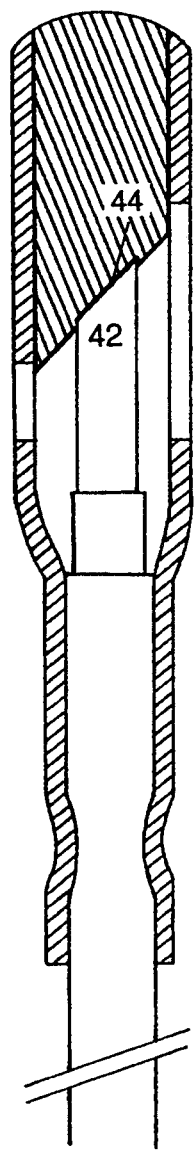
FIG. 4 is a cross section view of the transmitting end of another preferred embodiment of the invention, showing specifically the buried reflective end.

FIG. 4 is a cross section view of another preferred embodiment of the fiber tip of the laser delivery device of this invention. This embodiment, similar to that shown in FIG. 2, shows the bias cut fiber tip 42 buried slightly into a small recess 44 in the reflective surface. In this embodiment the reflective surface is on an insert encased within the cap. This buried tip prevents leakage of light and makes transmission of laser energy more precise.

Figure 5:
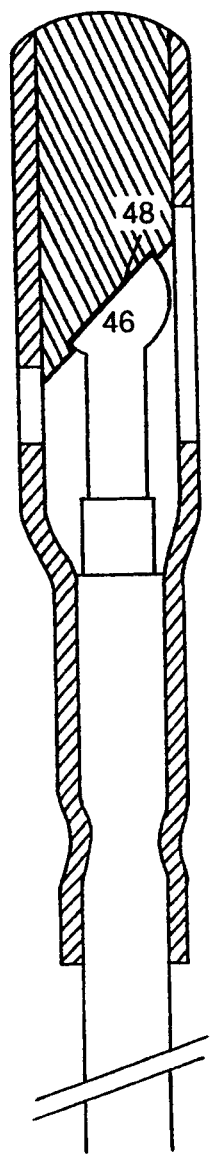
FIG. 5 is a cross section view of the transmitting end of another preferred embodiment of the invention, showing specifically the buried reflective end.

FIG. 5 is a cross section view of another preferred embodiment of the fiber tip of the laser delivery device of this invention. This embodiment, similar to that shown in FIG. 3, shows the bias cut fiber with a ball tip 46 buried slightly into a small recess 48 in the reflective surface. In this embodiment the reflective surface is on an insert encased within the cap. This buried tip prevents leakage of light and makes transmission of laser energy more efficient.

Figure 6:
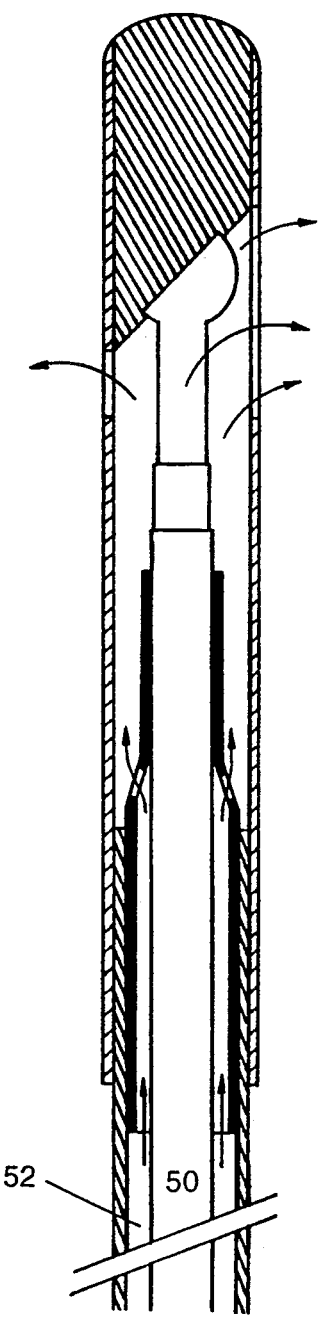
FIG. 6. is a cross section view of the transmitting end of another preferred embodiment of the invention, showing specifically the coaxial arrangement and irrigation flow pattern through the device.

FIG. 6 is a cross section view of another preferred embodiment of the fiber tip of the laser delivery device of this invention. This embodiment, similar to that shown in FIG. 3, shows the fiber 50 placed inside a coaxial cooling channel 52. This embodiment is used when there is a source of cooling or irrigation fluid such as $CO_2$ or saline. In operation, as the device is used, the cooling or irrigation fluid is pumped through the coaxial section of the device and flow is shown by the arrows in FIG. 6. This maintains low temperatures near the fiber tip. This embodiment is used in conjunction with a laser source utilizing a fiber tip temperature detection and protection system.

Figure 7:
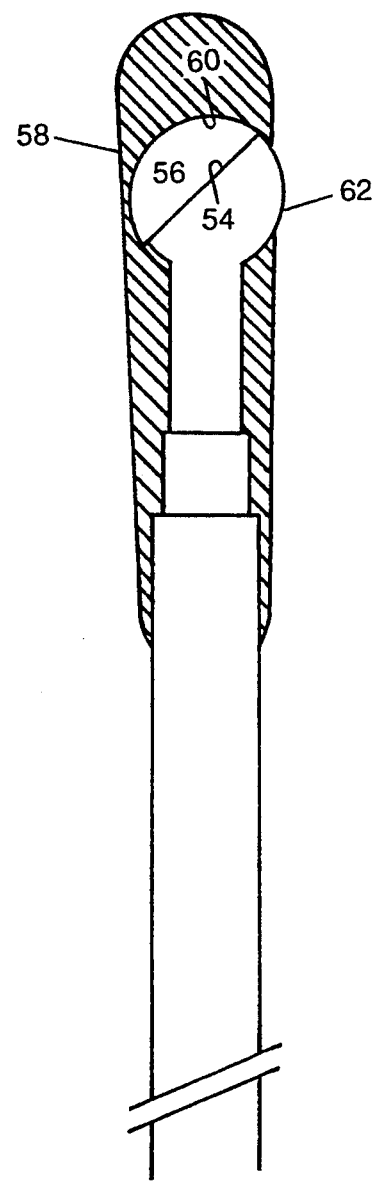
FIG. 7 is a cross section view of the transmitting end of another preferred embodiment of the invention, showing specifically the chamber or void between the end surface of the fiber and the reflecting cap.

FIG. 7 is a cross section view of another preferred embodiment of the fiber tip of the laser delivery device of this invention. As in FIG. 3, a ball-tip device with a bias cut polished fiber surface 54 is obtained. The surface might optionally be coated with an interference film. A pocket of air or other gas or fluid 56 is provided by an end cap portion 58 of the fiber tip. The inside surface 60 of the end cap could be provided with a highly reflective or mirrored surface. Thus, while most of the laser beam will be reflected off the bias cut end surface of the fiber itself, any stray beam impinging upon the inside surface of end cap will also be reflected out the side window 62 of the device with the rest of the reflected beam.

Figure 8:
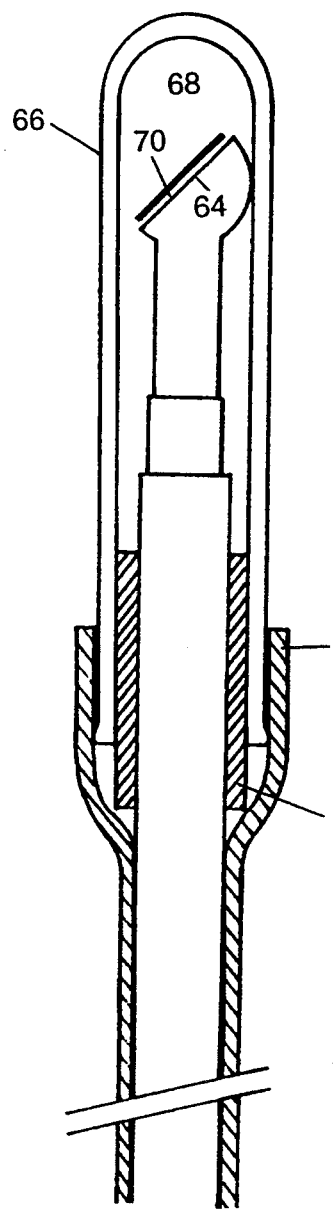
FIG. 8 is a cross section view of the transmitting end of another preferred embodiment of the invention, showing specifically the transmitting end of the fiber encased within a transparent shell and the bushing and connection between the fiber and the shell.

FIG. 8 is a cross section view of another preferred embodiment of the fiber tip of the laser beam delivery device of this invention. In this embodiment a bias cut end surface of a fiber 64 is enclosed within a sealed transparent shell 66. This shell may be made out of quartz, silica, pyrex or any suitable material transparent to laser light at any applicable wavelength and sufficiently heat resistant. The chamber 68 could be evacuated, filled with air or any other suitable fluid or gas which would result in beam reflection or refraction at predetermined angles. The bias cut fiber tip surface may also be coated with a reflective or interference film 70.

Also shown in FIG. 8 is a bushing 72 placed between the end of the transparent shell and the cladding 74 of the fiber. A piece of material 76 is clamped over the transparent shell to secure the assembly. This bushing connection provides increased mechanical integrity during operation, especially at elevated temperatures and when used with an irrigation or cooling system.

Figure 9:
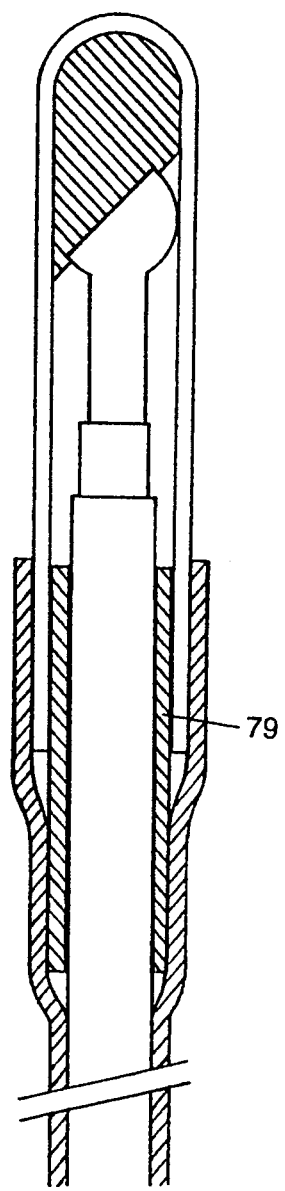
FIG. 9 is a cross section view of the transmitting end of another preferred embodiment of the invention, showing specifically the reflective insert in the transparent shell and the bushing and connection between the fiber and the shell.

FIG. 9 is a cross section view of another preferred embodiment of the fiber tip of the laser delivery device of this invention. In this embodiment a bias cut end surface of a ball tip fiber is in intimate contact with a reflective mirrored insert 78 with a recess to prevent leakage of light and consequential overheating. As in FIG. 8, the assembly is encased within a sealed transparent shell with a bushing 79.

Figure 10C:
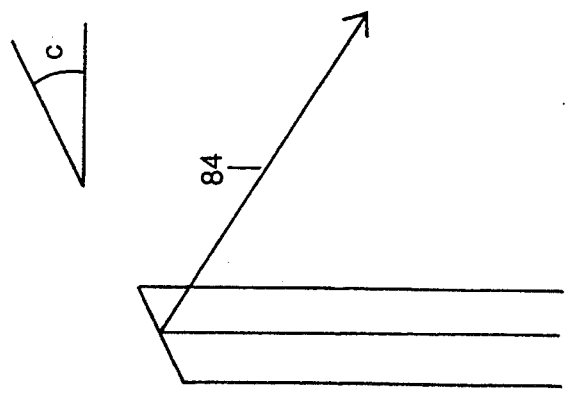
FIGS. 10A, 10B and 10C show cross sectional views of the bias cut end surface of the optical fiber whereby the end surface lies in a plane approximately equal to, greater than and less than, respectively, 45 degrees, with respect to the central axis of the fiber.
Figure 10B:
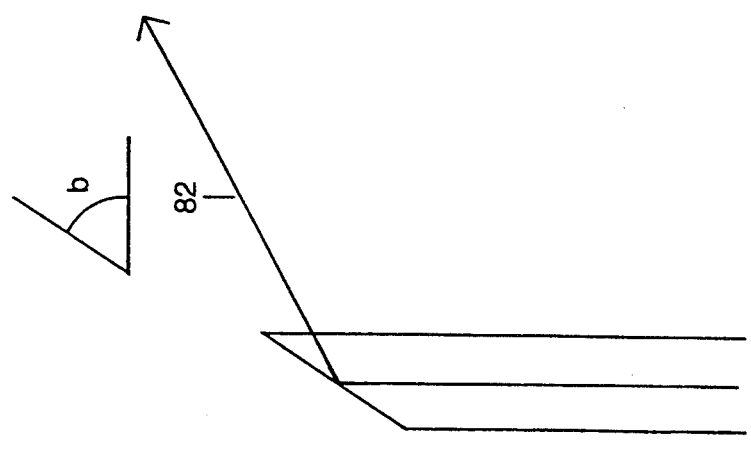
Figure 10A:
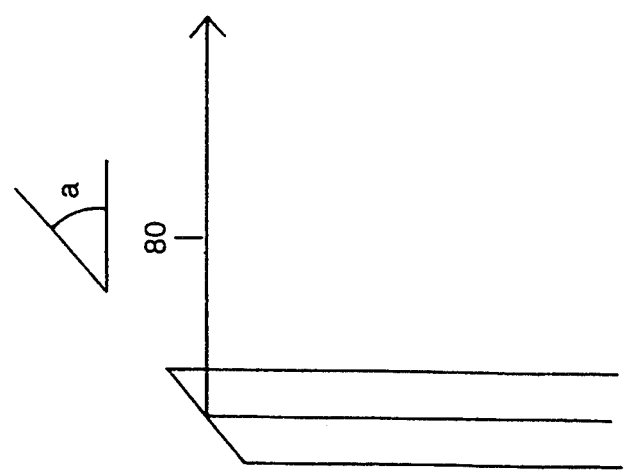

FIGS. 10A, 10B and 10C show cross sectional views of the bias cut end surface of the optical fiber whereby the end surface lies in a plane approximately equal to, greater than and less than, respectively, 45 degrees, with respect to the central axis of the fiber. In FIG. 10A the resultant beam path 80 is reflected to an angle of approximately 90 degrees with respect to the central axis of the fiber because the end surface lies in a plane at an angle a of approximately 45 degrees. In FIG. 10B the resultant beam path 82 is reflected to an angle greater than 90 degrees with respect to the central axis of the fiber because the end surface lies in a plane at an angle b which is greater than 45 degrees. In FIG. 10C the resultant beam path 84 is reflected to an angle less than 90 degrees with respect to the central axis of the fiber because the end surface lies in a plane at an angle c which is less than 45 degrees. Any of the embodiments of this invention, including those shown in FIGS. 2 through 9, can be constructed so as to deliver laser radiation to a wide range of predetermined angles. However, based on the characteristics of the fiber and the reflective surface or other media surrounding the tip of the fiber, there will be maximum and minimum angles for the bias cut end surface, outside of which the device will not function properly. If the angle of the bias cut end surface is too great with respect to the central axis of the fiber, then the laser energy may be refracted to the back of the firing tip rather than being reflected out the firing window, at least for certain embodiments. If the bias cut end surface is at an angle too small, then the reflected laser beam will be reflected backward, partially internally, and may have a destructive impact on the firing tip. Additionally, at angles other than somewhat greater than 45 degrees or somewhat less than 45 degrees, the efficiency of the reflection will decrease resulting in greater heat absorption by the firing tip and less efficient cauterizing, coagulating and ablating. Nevertheless, there is a wide range of angles at which the laser beam can be reflected to efficiently and precisely, both greater than and less than precisely transverse to the central axis of the optical fiber.

The embodiments of this invention can be used in almost all surgical operations for ablating, coagulating, incising or otherwise removing tissue. The different embodiments disclosed in the invention are also suitable for use in scientific, industrial, entertainment, communications and other commercial applications where angle delivery of laser beams at any wavelength via optical fibers is useful and applicable.

We claim:

1. A combination reflectance fiber optic laser beam angle delivery device, said device said device comprising:
   an optical fiber, said fiber having:
      a receiving end,
      a central axis, and
      a transmitting end, said transmitting end having a bias cut end surface, said end surface defining a predetermined operative angle with said central axis of said fiber;
   a reflecting cap, said transmitting end disposed within said reflecting cap, said reflecting cap further having at least one reflective surface such that said reflective surface is in intimate contact with said end surface of said fiber;
   and an attaching means securing said reflecting cap to said fiber.

2. The invention of claim 1 wherein said end surface lies in a plane at an angle of approximately 45 degrees to said central axis.

3. The invention of claim 1 wherein said end surface lies in a plane at an angle greater than 45 degrees with respect to said central axis.

4. The invention of claim 1 wherein said end surface lies in a plane at an angle less than 45 degrees with respect to said central axis.

5. The invention of claim 1 wherein said reflective surface consists of a dielectric material.

6. The invention of claim 1 wherein said reflective surface consists of a metallic material.

7. The invention of claim 1 wherein said reflective coating consists of a plurality of layers of different materials, said materials having different indices of refraction.

8. The invention of claim 1 wherein said reflecting cap further comprises a protective shell containing an insert member having said reflective surface.

9. The invention of claim 1 wherein said end surface of said fiber and the reflective surface are both contoured such that a beam with a predetermined beam pattern is delivered.

10. The invention of claim 1 wherein said fiber is enlarged proximate said transmitting end providing a truncated ball shaped transmitting end and an end surface with an increased area.

11. The invention of claim 1 wherein said reflective surface is provided with a recess such that said end surface of said fiber is disposed within said recess.

12. A combination reflectance fiber optic laser beam angle delivery device, said device comprising:
an optical fiber, said fiber having:
a receiving end,
a central axis, and
a transmitting end, said transmitting end having a bias cut end surface, said end surface defining a predetermined operative angle with said central axis of said fiber;
a reflecting cap, said transmitting end disposed within said reflecting cap, said reflecting cap having at least one reflective surface, said end surface being positioned adjacent to but not in physical contact with said reflective surface, thereby defining a chamber interposed between said end surface of said fiber and said reflective surface of said reflecting cap;
and an attaching means securing said reflecting cap to said fiber.

13. The invention of claim 12 wherein said chamber is filled with a fluid.

14. The invention of claim 12 wherein said chamber is filled with a gas.

15. The invention of claim 12 wherein said chamber is evacuated.

16. The invention of claim 12 wherein said end surface of said fiber further comprises a reflective layer such that said laser beam is internally reflected.

17. The invention of claim 1 wherein said fiber is disposed within a hollow coaxial channel delivering coolant fluid to the transmitting end of the fiber.

18. A combination reflectance fiber optic laser beam angle delivery device, said device comprising:
an optical fiber, said fiber having:
a receiving end,
a central axis, and
a transmitting end, said transmitting end having a bias cut end surface, said end surface defining a predetermined operative angle with said central axis of said fiber;
a fiber cap, said transmitting end disposed within and encased by said cap; and
a sealing means sealing said cap to said fiber such that a sealed chamber is created within said cap.

19. The invention of claim 18 wherein said chamber is filled with a fluid.

20. The invention of claim 18 wherein said chamber is filled with a gas.

21. The invention of claim 18 wherein said chamber is evacuated.

22. The invention of claim 18 wherein said end surface of said fiber further comprises a reflective layer such that said laser beam is internally reflected.

23. The invention of claim 22 wherein said reflective layer consists of a dielectric material.

24. The invention of claim 22 wherein said reflective layer consists of a metallic material.

25. The invention of claim 22 wherein said reflective layer consists of a plurality of layers of different materials, said materials having different indices of refraction.

26. The invention of claim 18 wherein said cap is made of glass transparent to said laser beam.

27. The invention of claim 18 wherein said cap is made of plastic transparent to said laser beam.

28. The invention of claim 18 wherein said fiber is enlarged proximate said transmitting end providing a truncated ball shaped transmitting end and an end surface with an increased area.

29. The invention of claim 18 wherein said cap further encases an insert member having a reflective surface thereon and wherein said fiber end surface is in intimate contact with said reflective surface.

30. The invention of claim 18 wherein said sealing means comprises a bushing disposed between said cap and said optical fiber.

* * * * *